United States Patent [19]

Umezawa et al.

[11] Patent Number: 4,612,285

[45] Date of Patent: Sep. 16, 1986

[54] NOVEL ANTITUMOR ANTIBIOTIC AWAMYCIN AND ITS PRODUCTION

[75] Inventors: Iwao Umezawa, Tokyo; Kanki Komiyama, Kanagawa, both of Japan

[73] Assignee: Kitasato Institute, Tokyo, Japan

[21] Appl. No.: 545,369

[22] Filed: Oct. 25, 1983

[30] Foreign Application Priority Data

Nov. 26, 1982 [JP] Japan .............................. 57-206087

[51] Int. Cl.$^4$ ..................... C12P 13/00; C12R 1/465; A61K 35/00; C07G 11/00
[52] U.S. Cl. .................................. 435/128; 424/120; 435/886; 536/16.8
[58] Field of Search ................ 424/120; 435/886, 128; 536/16.8

[56] References Cited

U.S. PATENT DOCUMENTS 3,997,663 12/1976 Pinnert et al. ...................... 424/120
4,207,313 6/1980 Umezawa et al. .................. 435/886

*Primary Examiner*—Charles F. Warren
*Assistant Examiner*—Rebecca L. Thompson
*Attorney, Agent, or Firm*—Ladas & Parry

[57] ABSTRACT

A novel antibiotic, awamycin, and its production. Awamycin is active against gram positive bacteria and exhibits growth inhibitory activity against Erhlich ascites and Sarcoma 180 cells. Some of the identifying characteristics of awamycin include a molecular weight of 744±1 (mass spectrum analysis), an elementary analysis of 59.16% C, 6.48% H and 1.88% N; a melting point of 158° C.; an optical rotation of $[\alpha]_D 24 = +836°$. Awamycin is an acidic substance, which provides an orange colored powder, and is poorly soluble in water.

2 Claims, 2 Drawing Figures

NOVEL ANTITUMOR ANTIBIOTIC AWAMYCIN AND ITS PRODUCTION

DETAILED EXPLANATION OF INVENTION

This invention relates to novel antitumor antibiotic awamycin and its production. More particularly, the present invention pertains the novel antibiotic awamycin which is produced by culturing antibiotic awamycin producing microorganism belonging to genus Streptomyces, exhibiting an antimicrobial activity against Gram positive bacteria and exhibiting growth inhibitory activity against Ehrlich ascites carcinoma cells and sarcoma 180 cells, or its salt and its production.

We have found that a microorganism strain 80-217 isolated from a soil sample collected at Minagawa-cho, Tochigi-ken, Japan, produces antibiotic substance active against Gram positive bacteria and exhibits growth inhibitory activity against Ehrlich ascites carcinoma cells and sarcoma 180 cells. We have also isolated and purified the said active substance from the said cultured broth and designated the said substance as novel antibiotic awamycin.

An object of the present invention is to provide an antibiotic awamycin having the physico-chemical properties hereinbelow illustrated.

Another object of the present invention is to provide a process for production of novel antibiotic awamycin which comprises culturing the antibiotic awamycin producing microorganism belonging to genus Streptomyces to accumulate antibiotic awamycin and isolating the antibiotic awamycin from the said cultured broth.

An antibiotic awamycin (hereinafter designates as awamycin) producing miroorganism belonging to genus Streptomyces, and the microorganism strain 80-217 belonging to genus Streptomyces isolated by the present inventors is preferable strain used in the present invention.

Taxonomical properties of the microorganism strain 80-217 are as follows.

a. Morphological properties:

Upon observation at 27° C. for 11 days on Waksman agar plate medium, the strain 80-217 has cylindrical aerial mycelia with scaly surface and sporangiophore of 0.78–0.95μ in length.

b. Growth conditions observed on various media at 27° C. for 14 days culture are as follows.

| Medium | Growth | aerial mycelia | reverse side | soluble pigment |
|---|---|---|---|---|
| yeast.malt extract agar | moderate | gray | brown | — |
| Oat meal agar | moderate | gray | gray | — |
| Starch inorganic agar | good | gray-white | yellowish brown | pale brown |
| Glycerol. asparagine agar | good | gray-white | pale brown | — |
| Peptone.yeast iron agar | moderate | pale brown-white | gold | — |
| Tyrosine agar | moderate | gray | pale brown | — |
| Nutrient agar | moderate | gray | gray | — |

—: trace soluble pigment (melanoid) or no formation.

c. Physiological properties:

(1) Growth temperature: 20°–37° C., optimum at 27° C., (2) Gelatine liquefaction (glucose-peptone-gelatine agar): positive, (3) Starch hydrolysis (starch-inorganic agar): positive, (4) Skim milk coagulation and peptonization (10% skim milk medium): weakly positive for peptonization, (5) Formation of melanin-like pigment (tyrosine agar medium and peptone-yeast extract-iron agar medium): negative, (6) $H_2S$ formation (peptone-yeast extract agar medium): negative, (7) Nitrite formation (nitrate medium): positive.

d. Assimiration of carbon sources (Pridham—Gottlieb agar medium, 27° C., 1–2 months):

| L-arabinose | ++ |
| D-xylose | + |
| D-glucose | ++ |
| D-fructose | ± |
| sucrose | — |
| inositol | — |
| L-rhamnose | + |
| raffinose | + |
| D-mannitol | — | e. Cell wall composition:

LL-type diaminopimelic acid is detected by a method of Becker et al. [Appl. Microbiol., 13, 236–243 (1965)].

As explained hereinabove, the strain 80-217 of the present invention belongs to genus Streptomyces. The strain has been deposited in Fermentation Institute, Agency of Industrial Science and Technology, MITI, Japan as deposition No. FERM P-6786.

Tge taxonomical properties of Streptomyces is, in general, easily mutated by natural or conventional artificial mutation, for example uv-irradiation, X-ray irradiation or chemical mutagens such as N-methyl-N-nitro-N-nitrosoguanidine or ethyl methanesulfonate. Mutant produced by artificial or natural mutation, which belongs to Streptomyces and has antibiotic awamycin producing activity, can be used in the present invention.

In the present invention, awamycin producing microorganism belonging to genus Streptomyces is cultured in a conventional medium for Streptomyces. Nutrient medium containing assimirable carbon sources, nitrogen sources and if necessary inorganic salt are used. Examples of assimilable carbon sources are glucose, sucrose, mannitol, molasses, starch, dextrin, cellulose, glycerol or organic acid in combination or individually. Examples of assimilable nitrogen sources are organic nitrogen such as peptone, meat extract, yeast extract, dry yeast, soy bean powder, corn steep liquor, cottonseed cake, caseine, soy bean protein hydrolysate, amino acid or urea, or inorganic nitrogen sources such as nitrate or ammonium salt, in combination or individually. Further, if necessary, inorganic salt such as sodium, potassium, calcium, magnesium or phosphate salt may be added. Other trace nutrients, growth stimulants or precursors may optionally be added to the medium.

Cultivation is carried out at aerobic condition such as shaking or aeration agitating culture. In an industrial production, submerged aeration culture is preferable. pH of the medium is preferably at acidic or meutral pH. Cultivation temperature is at 20°–37° C., usually at 24°–30° C., or preferably at 27° C. In a liquid culture, culturing time is usually for 4–6 days. Cultivation should naturally be stopped at maxium antibiotic production. These conditions can be altered depending upon a kind of strain used or other conditions. Antifoaming agent such as silicon oil, vegetable oil or surface active agent can also be added if required.

The thus produced antibiotic awamycin is accumulated in a cultured broth, and can be isolated from the culture filtrate by filtering the cultured broth with the aid of cellite or Hyflosupercel (trade name), or by centrifuge.

In order to isolate and purify the antibiotic awamycin, purification procedure applying the nature of the said antibiotic, being insoluble in hexane or petroleum ether, slightly soluble in water or diethyl ether and soluble in alcohol series solvent such as methanol or ethanol, chloroform series solvent such as acetone or methyl isobutyl ketone, ester series solvent such as ethyl acetate or butyl acetate, dimethylformamide or dimethyl sulfoxide can be used. In general, awamycin is transferred to organic solvent by extracting the culture filtrate with water immiscible organic solvent such as chloroform, methyl isobutyl ketone, ethyl acetate or butyl acetate preferably at pH 6.0-7.0.

The obtained organic layer is optionally washed with diluted ethylene diamine tetraacetate solution (EDTA) for isolating metal ion, then dehydrated with adding anhydrous sodium sulfate, anhydrous magnesium sulfate or beadgel. Dried organic layer is distilled off in vacuo. Though the awamycin is stable in heating, however the heating temperature at vacuum concentration is preferably controled below 60° C. Awamycin can be precipitated by adding hexane or petroleum ether to the residue. Precipitate is washed several times with hexane, filtered or centrifuged to obtain the crude awamycin. Further purification can be carried out by ion-exchange chromatography using ion exchange resin such as ion-exchange cellulose or ion-exchange Sephadex (trade name), adsorption chromatography using activated charcoal, silica-gel, alumina, hydroxyappatite, cellulose or adsorption resin such as HP-10, gel-chromatography using Sephadex or Biogel (trade name), electrophoresis, counter current distribution, ultrafiltration ior concentration, in combination thereof or individually. For example, the crude substance dissolved in a small amount of methanol, acetone, chloroform or benzene is charged on a column of silica-gel, eluted thereof with mixture of benzene-acetone and concentrated in vacuo the active fractions. Further, the concentrate dissolved in a small amount of chloroform, again charged on a column of silica-gel and eluted with chloroform-methanol. The active fractions are passed through a column of LH-20 Sephadex which is eluted with methanol and is chromatographed on a column of silica-gel, then eluted with benzene-methanol to purify the active substance.

Tge thus obtained awamycin is a basic substance and is formed as salt by conventional method.

Salt are pharmacologically acceptable salt, for example alkaline metal salt such as sodium or potassium, alkaline metal salt such as sodium or potassium, alkaline earth metal salt such as calcium or magnesium, or known organic amine salt.

Physico-chemical properties and biological properties of awamycin are as follows.

1. Physico-chemical properties:

(1) Elementary analysis: comprising carbon, hydrogen, oxygen and nitrogen; C: 59.16%, H: 6.48%, N: 1.88%, (2) Molecular weight: 744±1 (FD mass spectrum),
(3) M.P.: 158° C., (4) Specific rotation: $[\alpha]_D^{24} +836°$ (c=0.1, chloroform), (5) uv-spectrum: FIG. 1, $\lambda_{max}^{MeOH} (E_{1\ cm}^{1\%}) = 218$ nm (352), 245 nm (shoulder), 272 nm (shoulder), 340 nm (shoulder), 480 nm, $\lambda_{max}^{0.1\ N-NaOH/MeOH} = 225$ nm, 350 nm, (shoulder), 480 nm, (6) Infrared spectrum (KBr): FIG. 2, 3500-3400, 2900, 1730, 1660, 1620, 1480, 1460, 1438, 1403, 1370, 1290, 1250, 1210, 1170, 1142, 1105, 1080, 1060, 1040, 980, 970, 920, 880, 830, 790, 740, 700 cm$^{-1}$, (7) Solubility: insoluble: hexane and petroleum ether, slightly soluble: diethyl ether, soluble: alcohol series solvent such as methanol or ethanol, chlorinated methane series solvent such as dichloromethane or chloroform, ketone series solvent such as acetone or methyl isobutyl ketone, ester series solvent such as ethyl acetate or butyl acetate, benzene series solvent such as benzene or toluene, dimethylformamide or dimethyl sulfoxide, (8) Color reaction: positive: alkaline quinone reaction and magnesium acetate reaction (red purple), negative: Molisch's reaction and ninhydrin reaction, (9) Nature: acidic substance,

(10) Color: orange colored powder,

(11) Silica-gel TLC: carrier: silica-gel TLC plate (Merck), developer: benzene-methanol (5:1), Rf=approximately 0.5, 2. Biological proerties:

(1) Antimicrobial properties:

| test organisms | MIC μg/ml |
| --- | --- |
| *Staphylococcus aureus* FDA 209P | 0.8 |
| *Bacillus subtilis* PCI 219 | 0.1 |
| *Sarcina lutea* PCI 1001 | 0.05 |
| *Escherichia coli* NIHJ | >100 |
| *Shigella sonnai* | >100 |
| *Salmonella typhimurium* | >100 |
| *Klebsiella pneumonia* PCI 602 | >100 |
| *Pseudomonas aeruginosa* P-3 | >100 |
| *Saccharomyces sake* | >100 |
| *Candida albicans* | >100 |
| *Aspergillus nigar* | >100 |
| *Pyricularia oryzae* | >100 |
| *Trichophyton ferrugineum* | >100 |

As illustrated, awamycin shows antibacterial action against some of Gram positive bacteria, however no action against Gram negative bacteria, yeast and fungi.

(2) Antitumor activity:

(1) Effect on Ehrlich ascites carcinoma:

Ehrlich ascites carcinoma, 2×10$^6$ cells, is inoculated into mice (ddY, male, 6 weeks age) intra peritoneally, administered awamycin as shown in the table, number of survival dates is observed.

TABLE 1

| Administered (mg/kg/day) | Administering date | Number of survival date (median) | Increased life span (%) |
| --- | --- | --- | --- |
| Control | — | 22 | 0 |
| 6.3 | 1-9 | 38 | 73 |
| Control | — | 20 | 0 |
| 25 | 0, 1, | 40 | 100 |

Administered date is designates as 0th day at tumor inoculation date. Number of survival dates is shown as mean value in 4–5 mice in one group. Increased life span is calculated according to the following equation.

Increased life span (%) =

$$\frac{\text{mean value of number of survival date in administered group}}{\text{mean value of number of survival date in control group}} \times 100 - 100$$

(2) Effect on Sarcoma-180:

Sarcome-180 ($1 \times 10^5$ cells) is inoculated intra peritoneally in mice (ICR, male, 6 weeks age), administered the drug and the number of survival dates is observed.

TABLE 2

| Amount of administered (mg/kg/day) | Administering day | Number of survival dates (mean value) | Increased life span (%) |
|---|---|---|---|
| Control | — | 14 | 0 |
| 6.3 | 1–9 | 40 | 186 |
| 3.1 | 1–9 | >60 | >329 |
| 1.5 | 1–9 | 42 | 200 |
| 0.75 | 1–9 | 23 | 64 |
| Control | — | 12 | 0 |
| 25 | 0, 1, | 24 | 100 |

As illustrated hereinabove, awamycin has antitumor activity against Ehrlich and Sarcoma-180 ascites carcinoma.

Awamycin may have quinone structure in its molecule considering the above illustrated properties of uv-spectrum, IR-spectrum, color reactions and others. Heretofore, many antitumor substances having quinone structure have been known. Among known antibiotics having resembled elementary analysis and quinone structure, adriamycin, luraomycin and baracidine can be mentioned. However awamycin is different from these known substances as shown in Table 3.

TABLE 3

|  | m.p. | UV-absorption |
|---|---|---|
| Adriamycin | 205 | 233, 253, 290, 477, 475, 530 |
| Luraomycin | 151 | 280, 420–440 |
| Balacidine | 261 | 246, 294, 375 |
| Awamycin | 156 | 218, 245 (shoulder), 272, 340 (shoulder), 445 |

As illustrated, awamycin differs from the known antibiotics on melting points and uv-absorption.

Following examples illustrate the present invention but are not construed as limiting.

EXAMPLE 1

Shaking flask culture:

A liquid medium (medium A, pH 7.0, 100 ml) containing glucose 2.0%, peptone 0.5%, meat extract 0.5%, dry yeast 0.3%, NaCl 0.5% and calcium carbonate 0.3% in 500 ml Erlenmeyer flask was sterilized. A loopful Streptomyces 80-217 FERM P-6786 cultured at 27° C. for 6 days on agar slant medium containing glucose 1%, peptone 0.5%, meat extract 0.5%, NaCl 0.3% and agar 1.2%, was inoculated the above liquid medium, and shake cultured at 27° C. for 72 hours, at 120 reciplocation/minutes, amplitude 17 cm. Obtained cultured broth (2 ml) was inoculated into a liquid medium (medium B, 100 ml) containing glucose 0.2%, starch 1.5%, peptone 0.25%, meat extract 0.3%, dry yeast 0.15% and calcium carbonate 0.25% in 500 ml Erlenmeyer flask, and reciplocally shake cultured at 27° C. for 20 hours.

EXAMPLE 2

Cultivation in 30 lit. jar-fermenter:

A seed culture (100 ml × 5 flasks) obtained in example 1 was inoculated into a medium B (20 lit.) in 30 lit. jar-fermenter, and cultured at agitation 250 rpm, aeration 10 lit./min., at 27° C. for 20 hours.

EXAMPLE 3

Culture filtrate and extraction of active substance with ethyl acetate:

Ethyl acetate (30 lit.) was added in the cultured broth (30 lit. jar-fermenter × 2) obtained in example 2, stirred at 250 rpm by chemi-stirrer for 20 minutes, and separated the organic layer by sharpless type continuous centrifuge (18000 rpm). Ethyl acetate layer was filtered by suction. Extract was concentrated in vacuo to obtain oily substance.

EXAMPLE 4

Extraction of active substance with benzene:

Benzene (4 lit.) was added in the oily substance obtained in example 3, and further added aqueous solution (2 lit.) of 0.5% sodium EDTA therein, then stirred well. Aqueous solution (2 lit.) of 0.5% sodium EDTA was again added in separated benzene layer and stirred well. Benzene layer was separated.

EXAMPLE 5

Removal of oily impurities with hexane:

Anhydrous sodium sulfate was added in the benzene layer obtained in example 4 to dehydrated completely, and concentrated in vacuo. Hexane (100 ml) was added in the residue and the precipitated orange colored substance was separated by centrifuge (5 min., 2000 rpm). The precipitate was washed with hexane to obtain crude awamycin (100 mg).

EXAMPLE 6

Separation of awamycin by silica-gel chromatography (1):

Crude awamycin, obtained in example 5, dissolved in benzene (5 ml) was charged on a column (2.5 × 40 cm) of silica-gel 60 (Merck) placed with benzene, and washed with benzene (300 ml), subsequently eluted with benzene-methanol (10:1) (500 ml). Each fraction was checked by bioautography using Bacillus subtilis and active fraction were concentrated in vacuo to obtain orange colored substance.

EXAMPLE 7

Separation of awamycin by silica-gel chromatography (2):

Silica-gel 60 (Merck) was packed with chloroform in a column (2.5 × 40 cm). Orange colored powder obtained in example 6 dissolved in chloroform (5 ml) was charged on the column, washed with chloroform (300 ml) and eluted with chloroform-methanol (50:1) (500 ml). Each fraction was checked by bioautography using Bacillus subtilis and active fractions were concnetrated in vacuo to obtain orange colred powder.

EXAMPLE 8

Purification of awamycin by LH-20 sephadex-gel chromatography:

LH-20 sephadex (Pharmacia Fine Chem. Co.) packed with methanol in a column (1.45×45 cm). Orange colored powder, obtained in example 7, dissolved in methanol (1 ml) was charged on the column and eluted with methanol. Each fraction was checked by bioautography using *Bacillus subtilis* and the active fractions were concentrated in vacuo to obtain orange colored powder.

EXAMPLE 9

Separation of awamycin by silica-gel chromatography (3):

Orange colored powder, obtained in example 8, dissolved in a small amount of methanol was charged on a preparative silica-gel 60 thin layer plate (Merck, TLC plate 20×20 cm) at 3 cm distance from the edge. The dried band was developed with benzene-methanol (5:1). Active band was moved to approximately Rf=0.5 which was defined visually or checked by TLC scanner at 480 nm to define the pure band zone. The said band zone was carefully scratched by micro spatula and mixed with methanol and shke well. Methanol layer was separated by centrifuge (2000 rpm, 10 min.). Residual silica-gel was again shake well with methanol (3 ml). These extractions were repeated three times. The combined methanol layer was dried up in vacuo to obtain orange colored powder.

EXAMPLE 10

Purification of awamycin by chloroform-hexane (1:10):

Orange colored powder obtained in example 9 was dissolved in chloroform (5 ml). Hexane (50 ml) was added thereto, stirred well and allowed to stand in a refrigerator ($-20°$ C.) for 2-3 days. Orange colored precipitate was separated by centrifuge (2000 rpm, 5 min.) at $-20°$ C., and dried in vacuo to obtain purified awamycin (10 mg).

Figure 1:
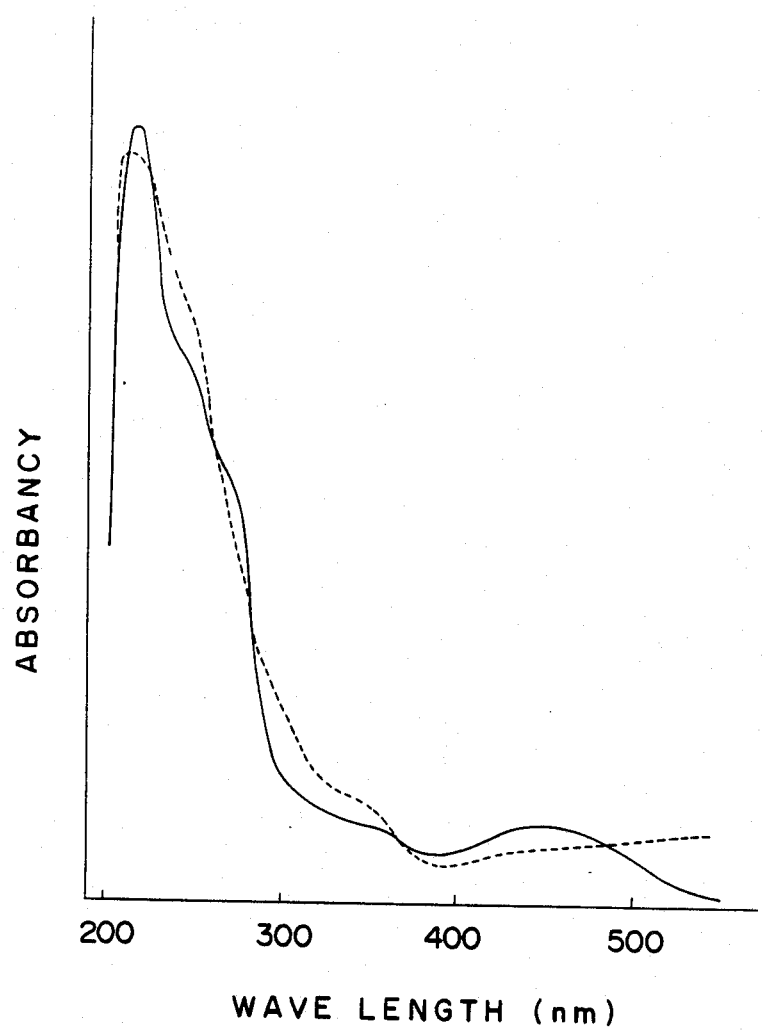
FIG. 1: uv-spectrum of awamycin.
Figure 2:
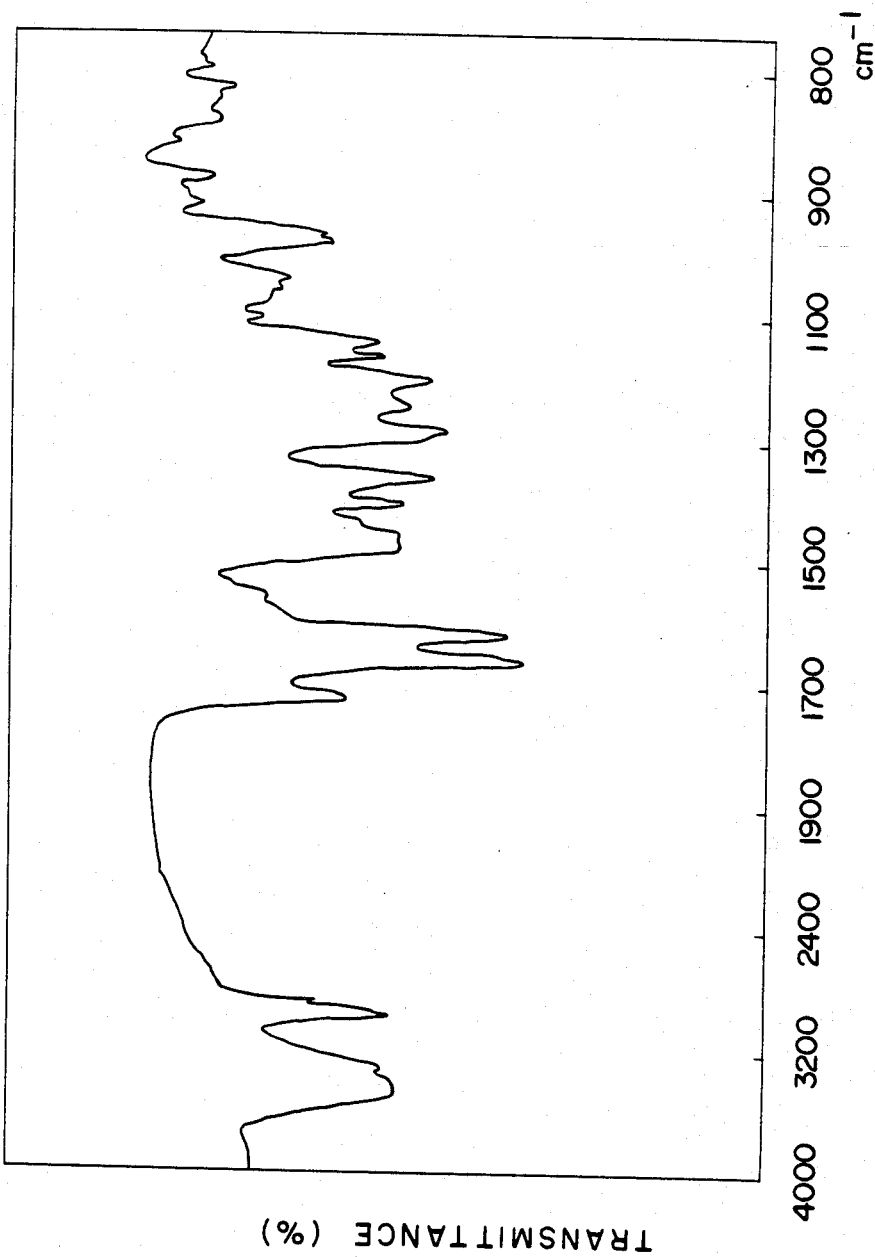
FIG. 2: IR-spectrum of awamycin.

We claim:

1. An antibiotic awamycin having the following physicochemical properties;
   (1) Elementary analysis:
      comprising corbon, hydrogen, oxygen and nitrogen,
      C: 59.16%, H: 6.48%, N: 1.88%
   (2) Molecular weight: 744±1 (mass spectrum analysis),
   (3) Melting point: 158° C.,
   (4) Optical rotation: $[\alpha]_D^{24} = +836°$ (c=0.1, chloroform),
   (5) Ultraviolet absorption spectrum: shown in FIG. 1,
   (6) Infrared absorption spectrum: shown in FIG. 2,
   (7) Solubility:
      insoluble in hexane and petroleum ether, difficultly soluble in water and diethyl ether, and
      soluble in methanol, ethanol, dichloromethane, chloroform, acetone, ethyl acetate, benzene and dimethylformamide,
   (8) Color reactions:
      positive for alkaline quinine reaction (violet) and magnesium acetate reaction (red purple),
      negative for Molisch and ninhydrin reaction,
   (9) Nature: acidic substance, and
   (10) Color: orange colored powder.

2. A process for production of antibiotic awamycin which comprises culturing antibiotic awamycin producing microorganism Streptomyces strain 80-217 Ferm P-6786 in a medium, accumulating the antibiotic awamycin and isolating antibiotic awamycin from the cultured broth, wherein the antibiotic awamycin has the following properties:
   (1) Elementary analysis:
      comprising corbon, hydrogen, oxygen and nitrogen,
      C: 59.16%, H: 6.48%, N: 1.88%
   (2) Molecular weight: 744+1 (mass spectrum analysis),
   (3) Melting point: 158%° C.,
   (4) Optical rotation: $[\alpha]_D^{24} = +836°$ (c=0.1, chloroform),
   (5) Ultraviolet absorption spectrum: shown in FIG. 1,
   (6) Infrared absorption spectrum: shown in FIG. 2,
   (7) Solubility:
      insoluble in hexane and petroleum ether, difficulty soluble in water and diethyl ether, and
      soluble in methanol, ethanol, dichloromethane, chloroform, acetone, ehtyl acetate, benzene and dimethylformamide,
   (8) Color reactions:
      positive for alkaline quinone reaction (violet) and magnesium acetate reaction (red purple),
      negative for Molisch and ninhydrin reaction,
   (9) Nature: acidic substance, and
   (10) Color: orange colored powder.

* * * * *